(12) United States Patent
Sabin (10) Patent No.: US 11,510,932 B2
(45) Date of Patent: Nov. 29, 2022

(54) PROPHYLACTIC AND THERAPEUTIC TREATMENT OF ALZHEIMER'S DISEASE USING PHYTIC ACID AND PHYTATE TO REDUCE AMYLOID BETA PLAQUE AND TAU PROTEIN

(71) Applicant: Robert Sabin, Mill Neck, NY (US)

(72) Inventor: Robert Sabin, Mill Neck, NY (US)

( * ) Notice: Subject to any disclaimer, the term of this patent is extended or adjusted under 35 U.S.C. 154(b) by 141 days.

(21) Appl. No.: 17/064,536

(22) Filed: Oct. 6, 2020

(65) Prior Publication Data

US 2021/0038618 A1 Feb. 11, 2021

Related U.S. Application Data

(63) Continuation of application No. 12/661,964, filed on Mar. 26, 2010.

(60) Provisional application No. 61/273,126, filed on Jul. 29, 2009, provisional application No. 61/211,230, filed on Mar. 27, 2009.

(51) Int. Cl.
*A61K 31/6615* (2006.01)
*A61P 25/28* (2006.01)
*A61K 31/66* (2006.01)
*A61K 9/00* (2006.01)
*A61K 9/20* (2006.01)
*A61K 9/19* (2006.01)

(52) U.S. Cl.
CPC ........ *A61K 31/6615* (2013.01); *A61K 9/0014* (2013.01); *A61K 9/0021* (2013.01); *A61K 9/0095* (2013.01); *A61K 9/19* (2013.01); *A61K 9/2004* (2013.01); *A61K 31/66* (2013.01); *A61P 25/28* (2018.01)

(58) Field of Classification Search
CPC ........................... A61K 31/6615; A61P 25/28
See application file for complete search history.

(56) References Cited

U.S. PATENT DOCUMENTS

| 4,758,430 A * | 7/1988 | Sabin ...................... A61K 31/66 514/23 |
|---|---|---|
| 4,847,082 A | 7/1989 | Sabin |
| 2006/0014716 A1 | 1/2006 | Frey II |
| 2006/0106001 A1 | 5/2006 | Coppolino |

OTHER PUBLICATIONS

Grases et al., "Intracellular and extracellular myo-inositol hexakisphosphate (InsP6), from rats to humans," Anticancer Res. May-Jun. 2005;25(3c):2593-97. PMID: 16080499. (Year: 2005).*

(Continued)

*Primary Examiner* — Theodore R. Howell
(74) *Attorney, Agent, or Firm* — Alfred M. Walker; Jennifer Yancy; John F. Vodopia (57) ABSTRACT

A composition and method for the treatment of Alzheimer's disease and related amyloid plaque development and reduction of amyloid plaque, amyloidosis and amyotrophic lateral sclerosis, includes an effective amount of a compound selected from the group consisting of phytic acid, a phytate salt, an isomer or hydrolysate of phytic acid or a phytate salt, or a mixture of any combination thereof, being administered to a person in an amount from about 0.5 grams to about 18.75 grams per day.

13 Claims, 6 Drawing Sheets

(56) References Cited

OTHER PUBLICATIONS

Cavazzoni, Dr. Patrizia; "FDA's Decision to Approve New Treatment for Alzheimer's Disease"; FDA Center for Drug Evaluation and Research, Food & Drug Administration; Jun. 7, 2021, Food and Drug Administration 10903 New Hampshire Ave, Silver Spring, MD 20993-0002.

"Lilly's donanemab receives U.S. FDA's Breakthrough Therapy designation for treatment of Alzheimer's disease"; Eli Lilly and Company PR Newswire; Jun. 24, 2021; Indianapolis, IN.

Anderson, Maia; "Eli Lilly asks FDA to authorize its Alzheimer's drug"; Oct. 26, 2021; Becker's Healthcare Podcasts.

Okuda, Michiaki, et al.; Highly water pressurized brown rice improves cognitive dysfunction in β-senescence-accelerated mouse prone 8 and reduces amyloid beta in the brain; BMC Complementary and Alternative Medicine (2018) 18:110; https://doi.org/10.1186/s12906-018-2167-z.

Larvie, Doreen Y., Arjah, Seth M.; "Estimated Phytate Intake Is Associated with Improved Cognitive Function in the Elderly, NHANES 2013-2014."; Antioxidants 2021, 10, 1104. Licensee: MDPI, Basel, Switzerland; published Jul. 10, 2021; https://doi.org/10.3390/antiox10071104.

Abe, Takako K., Taniguchi, Masayuki; Identification of myo-inositol hexakisphosphate (IP6) as a β-secretase (BACE1) inhibitory molecule in rice grain extract and digest; Department of Materials Science and Technology, Faculty of Engineering, Niigata University, Ikarashi 2-8050, Niigata 950-2181, Japan; Accepted Jan. 25, 2014, Elsevier B. V., http://dx.doi.org/10.1016/j.fob2014.01.008.

Abdulwaliyu, Ibrahim, et al.; "Investigation of the medicinal significance of phytic acid as an indispensable anti-nutrient in diseases"; European Society for Clinical Nutrition and Metabolism; Published by Elsevier Ltd.; Accepted Oct. 12, 2019; https://doi.org/10.1016/j.yclnex.2019.10.02.

\* cited by examiner

PROPHYLACTIC AND THERAPEUTIC TREATMENT OF ALZHEIMER'S DISEASE USING PHYTIC ACID AND PHYTATE TO REDUCE AMYLOID BETA PLAQUE AND TAU PROTEIN

RELATED APPLICATIONS

This application claims priority from provisional application number 61/211,230 filed Mar. 27, 2009 and provisional application number 61/273,126, filed Jul. 29, 2009 and claims benefit and priority under 35 U.S.C. § 119(e). These applications are incorporated by reference herein.

All Patents, Scientific Articles, and other Documents mentioned herein are incorporated by reference as if reproduced in full below.

FIELD OF THE INVENTION

This invention relates to the prophylactic and therapeutic treatment of Alzheimer's Disease, herein-below identified as "AD".

BACKGROUND OF THE INVENTION

Phytic acid, generally accepted as having the structure myo-inositol-hexakis (dihydrogen phosphate), is a major component of plant seeds, constituting 1-3% by weight of many cereals and oil seeds. Most wheat brans contain between 4 and 5% phytic acid. Phytic acid may be prepared in pure form from various plant sources, such as wheat, corn, soybeans, sesame seeds, peanuts, lima beans, barley, oats, wild rice and sunflower seeds. It can be extracted with dilute hydrochloric acid at room temperature, precipitated with various reagents including ferric chloride, bicarbonates, potassium hydroxide, sodium hydroxide, ammonium hydroxide, calcium hydroxide, magnesium hydroxide or alcohol. It is then further purified by conventional chemical techniques.

When one or more of the acidic protons of the phosphate groups in phytic acid are replaced by a counterion, the compound is usually referred to as a phytate salt. The special name phytin is used for the calcium-magnesium salt of phytate derived from plant seeds (a product of Ciba-Geigy). The present invention includes the use not only of phytic acid and phytate salts, but also various isomeric forms of phytic acid and phytate salts. While the Anderson structure for myo-inositol hexakis dihydrogen phosphate is the accepted structure for phytic acid, the present invention covers other isomers which have been previously described in the literature. These isomers include the cis, epi, allo, muco, neo, D-chiro, L-chiro, and scyllo configurations.

Also, while phytic acid contains six phosphate groups, when introduced into the digestive tract of an animal, one or more of the phosphate groups may be hydrolyzed by the action of the digestive acids and enzymes. Therefore, the present invention includes the use of hydrolysates of phytic acid and phytate salts wherein one or more of the phosphate groups have been removed.

The main uses of phytic acid include use as a food additive for preservation of foods. Studies on the use of phytic acid as a food additive show that ingestion of large doses of phytic acid elicits no physiological discomfort or symptoms of any toxicological action in humans. See Starkenstein, Biochem. Z. 30: 56 (1911). Phytic acid and its metabolites are thus not believed to be toxic or highly reactive.

Phytic Acid is the 6 phosphates ester of inositol. Inositol, chemically hexahydroxycylohexane, is any of nine stereoisomeric alcohols that closely resemble glucose in structure. It is a constituent of many cell phosphoglycerides. Meso- or myo-inositol, named for its presence in muscle tissue, is biologically the important isomer. Myo-inositol is the precursor in the phosphatidylinositol cycle, a source of two second messengers (diacylglycerol and inositol triphosphate). Inositols and their phosphates lack a hydrolytically labile glycosidic linkage and are stable to degradative enzymes in vivo. They have been used in the stable insulin mediators, inhibitors, and modulators. The phytic acid may be in a salt form, such as, for example, calcium magnesium phytate salt.

Two reports from Science Magazine of 3 Nov. 2006 support the importance of reducing Abeta plaque production as a therapeutic goal. See Goedert and Spillantini "A Century of Alzheimer's Disease", SCIENCE, Vol. 314, 3 Nov. 2006, pp 779-781. See also Roberson and Mucke, "100 Years and Counting: Proposals for Defeating Alzheimer's Disease," SCIENCE, Vol. 314, 3 Nov. 2006, pp. 781-784.

U.S. Pat. No. 4,847,082 (referred to herein as the '082 patent) and U.S. Pat. No. 4,758,430 (referred to herein as the '430 patent) both to Sabin, each of which is expressly incorporated herein by reference, disclose one embodiment for administration of phytic acid or equivalent phytate salt, isomer or hydrolysate as about one-half to three grams per kilogram of body weight orally per day.

Scyllo inositol, has been shown to prevent and reverse Alzheimer's Disease in a transgenic mouse model of Alzheimer's Disease (See Nature Medicine article) (See "A Sweet Solution to Alzheimer's Disease") (See "ALD103 May Prevent and Reverse Alzheimer's Disease") (See "Scyllo-Inositol Appears Promising for Alzheimer's Disease").

Scyllo inositol also inhibits and blocks the aggregation of amyloid-B peptide (AB) in these same transgenic Alzheimer Disease mouse studies. The '082 patent discloses scyllo inositol as an isomeric form of phytic acid. Since the '082 and '430 patents disclose a minimum oral dose of about a half a gram per kilogram/body weight per day, a 75 kilogram AD patient, would take 37.5 grams of scyllo inositol orally per day. This dose is burdensome. Additionally, phytate in food has been successfully consumed at this dose and higher.

Scyllo inositol is also disclosed in U.S. patent application Ser. No. 10/787,621 of McLaurin. This application discloses a litany of compounds for the treatment of disorders of protein aggregation, the most preferred compound of which is scyllo inositol.

SUMMARY OF THE INVENTION

Phytic acid, phytate salt, an isomer or hydrolysate of phytic acid or a phytate salt, or a mixture of any combination thereof is administered as a treatment for prevention and treatment of Alzheimer's disease and for treatment of amyloidosis, aggregation of beta amyloid proteins and tau protein in the brain.

An effective yet surprisingly low dose of the compounds phytic acid, phytate salt, an isomer or hydrolysate of phytic acid or a phytate salt, or a mixture of any combination thereof, except for scyllo inositol, are used for as a prophylactic and therapeutic treatment for Alzheimer's Disease. In a preferred embodiment, a dose of about 0.5 gram to about 18.75 gms of phytic acid, phytate salt, an isomer or hydrolysate of phytic acid or a phytate salt, or mixture of any combination thereof, except for scyllo inositol, are administered orally per day. This dose is 1/75th to one half (½) of the previously disclosed doses in the Sabin patents cited above Phytate salt may also he administered as a capsule, and the calcium magnesium phytate salt, as packaged by many suppliers such as Jarrow Formulations; is desirable.

Surprisingly, it has been discovered that very low doses of phytic acid, phytate salt, an isomer or hydrolysate of phytic acid or a phytate salt, or a mixture of any combination thereof are effective in the treatment and prevention of aggregation of beta amyloid proteins as are commonly seen in the brains of Alzheimer's patients. Treatment with such a low dose of phytic acid, phytate salt, an isomer or hydrolysate of phytic acid or a phytate salt, or a mixture of any combination thereof prevents the occurrence of potential side effects observed with high dose treatments and allows for ease of administration to Alzheimer's patients who may find it difficult to take high doses of the substance. Furthermore, it has been discovered that phytic acid, phytate salt, an isomer or hydrolysate of phytic acid or a phytate salt, or a mixture of any combination thereof is much more effective than scyllo inositol and myo inositol.

In one embodiment there is disclosed a composition for the treatment of Alzheimer's disease and related amyloid plaque development by providing a person in need thereof with an effective amount of phytic acid, phytate salt, an isomer or hydrolysate of phytic acid or a phytate salt, or a mixture of any combination thereof.

In another embodiment, there is disclosed a method for the treatment of Alzheimer's disease and the amyloid plaque protein aggregation by the oral administration of 0.5 to 18.75 grams of phytic acid, phytate salt, an isomer or hydrolysate of phytic acid or a phytate salt, or a mixture of any combination thereof per day. Alternatively, the compounds of the invention may be administered topically as a cream, ointment, gel and the like, transdermally or intradermally.

For a better understanding of the present invention, together with other and further objects, reference is made to the following description, taken in conjunction with the examples, and its scope will be pointed out in the appended claims.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION

The method according to the present invention comprises treating a subject, afflicted with Alzheimer's Disease, with a composition in which the active ingredient is phytic acid, a phytate salt, or an isomer or hydrolysate of phytic acid or phytate salt. By the term isomer as used herein, it is intended to include the various conformations of phytic acid, as described hereinabove, and the corresponding conformations of phytate salts. The term salts is broadly intended to cover any of the various salts formed by the replacement of any or all of the available acidic protons of the phosphate groups with a counterion. The counterion may be any pharmaceutically acceptable counterion such as sodium, magnesium, potassium, zinc, ferric, ferrous, and the like, including organic counterions such as quaternary ammonium ions and ions of organic bases.

The present invention also includes the hydrolysates of phytic acid and phytate salts wherein one or more of the phosphate groups have been removed. Once administered into the digestive tract, bloodstream, the phytic acid or phytate salt may be hydrolyzed by digestive, blood or cellular enzymes, thereby removing one or more of the phosphate groups on the cyclohexane ring. However, it is contemplated to be within the scope of the invention that these hydrolysates of phytic acid and phytate salts may also be administered directly to the subject and therefore are within the scope of the present invention.

The hydrolysates of phytic acid and phytate salts may be prepared by partial acid or basic hydrolysis or by hydrolysis using enzymes prior to preparation of dosage forms for administration. Preferably, the hydrolysates will be made in vivo by coadministering with phytic acid or phytate salt an enzyme which hydrolyzes phosphate groups, such as 3-phytase, 6-phytase or acid phosphatase.

The phytic acid or phytate salt may be absorbed into or adsorbed onto a solid carrier to facilitate pharmaceutical administration. For example, phytic acid may be formulated into a starch powder by spray drying or vacuum drying an aqueous mixture of phytic acid and dextrin.

The preferred compositions for administration, particularly in oral dosage form, are the mono-, di-potassium phytate salts and mixtures thereof which may be prepared from commercially and readily available sodium phytate by initially removing the sodium using ion exchange chromatography on a suitable resin, such as Dowex beads. The free phytic acid may then be treated with potassium hydroxide to convert to the mono- and di-potassium phytate salt.

The preferred method of administration of the compositions according to the present invention is through oral administration in liquid or tablet form. As described hereinabove, the compositions may be administered as pharmaceutically acceptable salts such as salts with alkali metal cations (sodium, potassium, lithium), ammonium salts and salts with organic bases such as piperidine, triethanolamine, diethylaminoethylamine salts, and the like.

In addition to the active ingredients, the composition may also contain an effective proportion, usually from 0.001 to 0.1% weight by volume, of a pharmaceutically acceptable preservative or sterilizing agent such as cetyl pyridinium chloride, tetradecyltrimethyl ammonium bromide (commercially known as Centramide), benzyl dimethyl [2-(2-)p-(1, 1,3,3-tetramethyl butyl)) phenoxy) ethoxyl] ammonium chloride (known commercially as Benzethonium Chloride) and myristyl-gamma-picolinium chloride.

The pharmaceutical composition may also contain conventional excipients, e.g., sodium chloride, dextrose, mannitol, and buffers such as sodium dihydrogen ortho phosphate, disodium hydrogen phosphate, sodium citrate/citric acid, and boric acid/sodium borate. The proportion and concentration of excipients and buffers may be varied within fairly wide ranges, providing the resulting solution is stable and nonirritating when administered. The preferred method of administration is by oral administration as a solid compound. The composition may be prepared in the conventional manner as tablets, pills or powders, using conventional carriers.

The phytic acid may be combined with other inactive substances as are known in the pharmaceutical arts such as, for example, lactates, silicates, and magnesium stearate, as well as with other active substances, such as pharmaceutical drugs and vitamins, etc.

For oral administration, in a preferred embodiment, the active ingredient of the composition will also contain an enzyme such as 3-phytase (EC 3.1.38), 6-phytase (EC 3.1.3.26) or acid phosphatase which, when exposed to the digestive tract, will assist in hydrolyzing one or more of the phosphate groups from the active ingredient. Since phytic acid or phytate salts are not naturally present in animals, the digestive enzymes in animals are believed to be insufficient to completely hydrolyze the phosphate groups. Therefore, to enhance the hydrolysis of the phosphate groups in an animal or man, it is preferred that the active ingredient be administered with one or more of the aforementioned enzymes, with the preferred enzyme being 3-phytase (EC 3.1.38).

The phytic acid, phytate salt, an isomer or hydrolysate of phytic acid or a phytate salt, or a mixture of any combination thereof can be administered in any manner as known in the art. In one embodiment the phytic acid is administered orally in encapsulated form. The oral administration can be in the form of a capsule, quick dissolve tablet, table, or other form as known in the art. The dosage of phytic acid is an amount that is effective for the disease state of the Alzheimer's patient and an amount effective as a prophylactic treatment for prevention of Alzheimer's disease. In one embodiment the dosage is from orally about 0.5 g to about 18.75 g of phytic acid, phytate salt, an isomer or hydrolysate of phytic acid or a phytate salt, or a mixture of any combination thereof per day.

The present invention can be better understood by reference to the following examples. The following examples illustrate the present invention and are not intended to limit the invention or its scope in any manner.

EXAMPLES

The Applicant tested compounds disclosed in the above referenced patents of Sabin using well established standard routine testing, as known in the art, at Oregon Science and Health University in an in-vitro challenge test.

The Applicant submits two pages of the data of these in vitro tests. in the first test, phytic acid attenuates APP CTF-induced neurotoxicity. APP is a precursor/source to beta amyloid plaque and is considered by many to be a "bad actor", "cause", of Alzheimer's Disease. See DDN BENCH PRESS. Neither scyllo inositol nor myo inositol previously used by Barak et al, "inositol treatment of Alzheimer's disease: a double blind, cross-over placebo controlled trial", Prog. Neuro-Psychopharmacol. & Biol. Psychiatry., 20(4): 729-735, 1996 attenuated APP CTF-induced neurotoxicity. Phytic acid is shown to be active, while scyllo inositol and myo inositol are shown to be inactive. These surprising and unexpected results with phytic acid attenuating APP CTF-induced neurotoxicity, while scyllo inositol and myo inositol fails in these same tests, suggests that phytic acid would be effective as a treatment for Alzheimer's Disease at a surprising, unexpected, non-obvious, severely reduced dose, as against the previously cited claimed dosages in the Alzheimer's Treatment Patents, especially since phytic acid proved scyllo inositol inactive in this in vitro challenge test. These results from this in vitro test demonstrate superiority over scyllo inositol and myo-inositol; and demonstrate novelty and reduction to practice for the prophylactic and therapeutic treatment of Alzheimer's disease.

In vitro studies were conducted in MC65 cells, an established human neuroblastoma line that conditionally expresses the first 17 amino-terminal residues and the 99 carboxy-terminal residues of amyloid precursor protein (APP CTF). Detectable APP CTF expression occurs within 3-4 h of tetracycline withdrawal, appearance of aggregates and initial losses of culture viability occurs at about 2 days and near complete death occurs by approximately 3 days.

Phytic Acid Attenuates APP CTF-Induced Neurotoxicity

Phytic acid protected the cells from APP CTF-induced death in a concentration dependent manner with an $EC_{50}$ concentration of approximately 100 μM and concentrations of 200 μM and higher providing near complete protection from cytotoxicity. Treatment with 100 μM phytic acid suppressed oxidative stress associated with APP CTF expression, as measured by concentrations of hydrogen peroxide in the cell media Scyllo- and Myo-Inositol Do Not Rescue Cells from Ab-Induced Neurotoxicity Stereoisomers of cyclohexanehexol—(the parent compound of phytic acid) protect primary cultured neurons from Ab oligomer-induced cytotoxicity and prevent/reverse Alzheimer phenotype in a mouse model {McLaurin, 2006 #103}, {McLaurin, 2000 #104}. To test the specific of phytic acid's effects on Mc65 cells, cells were treated with the cyclohexanehexol isomers scyllo and myo-inositol at doses of 10 μM (a dose that rescues NGF-differentiated PC12 cells from Ab-induced neurotoxicity) {McLaurin, 2000 #104} and 100 mM (the $EC_{50}$ of phytic acid). Neither isomer rescued MC65 cells from APP CTF-induced cytotoxicity.

IN VIVO TEST RESULTS

Figure 1:
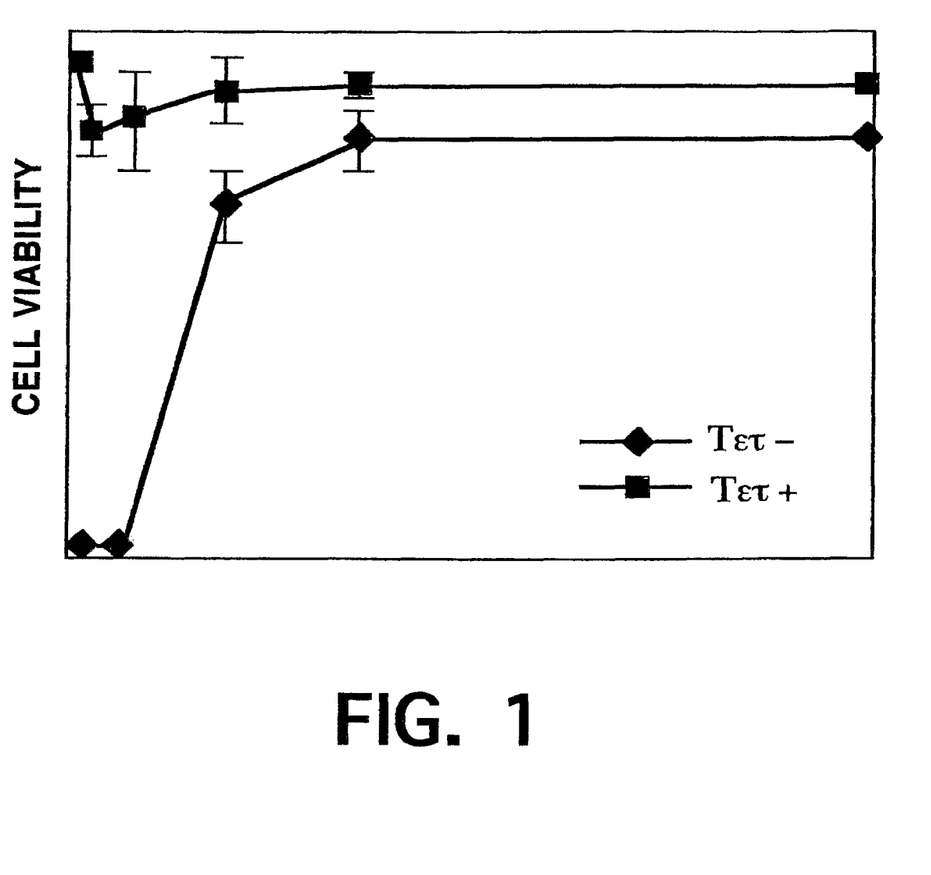
FIG. 1 is a chart of cell viability.
Figure 2:
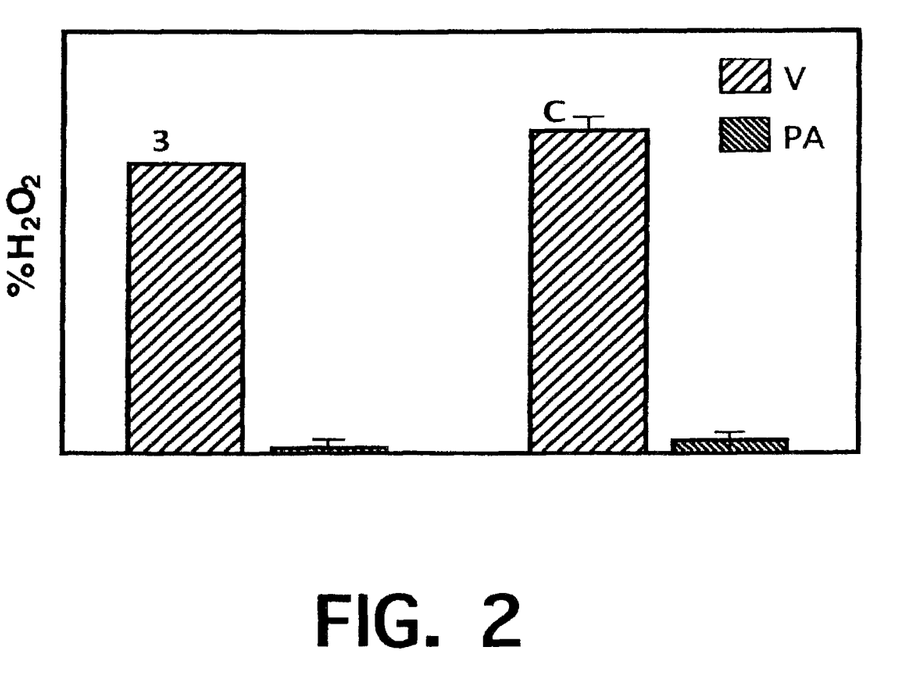
FIG. 2 is a chart of a bar graph of the percentage of $H_2O_2$, where V=control and PA=phytic acid.
Figure 3:
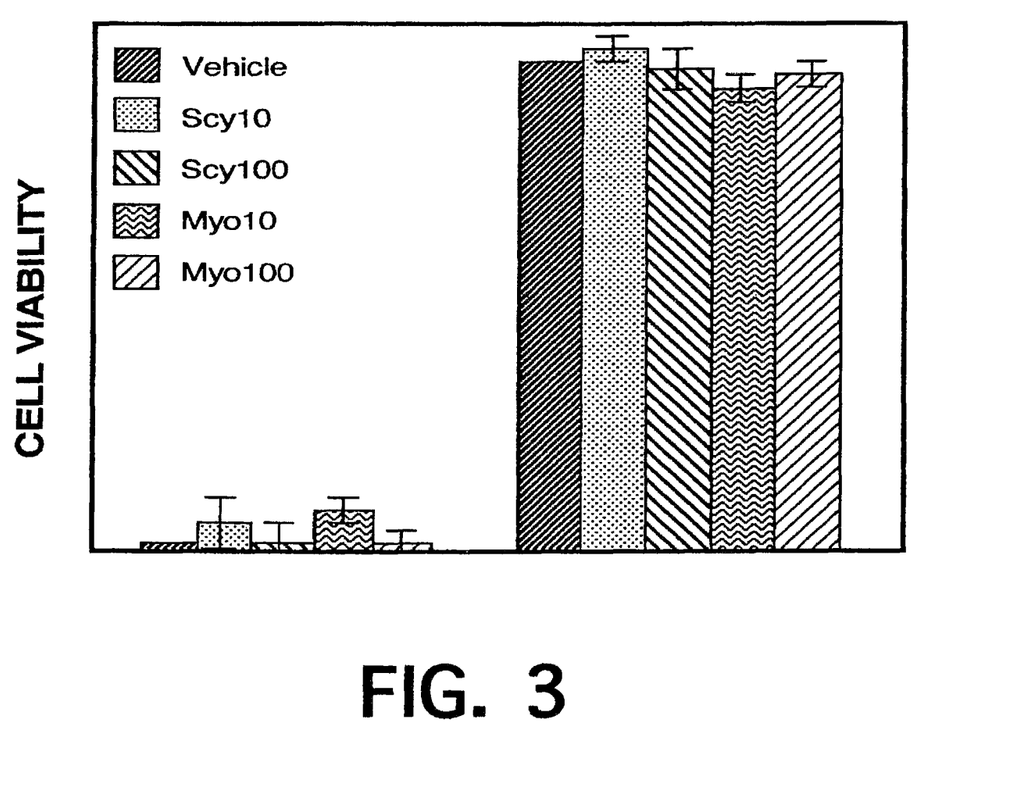
FIG. 3 is a chart of cell viability of scyllo inositol and myo inositol.
Figure 4:
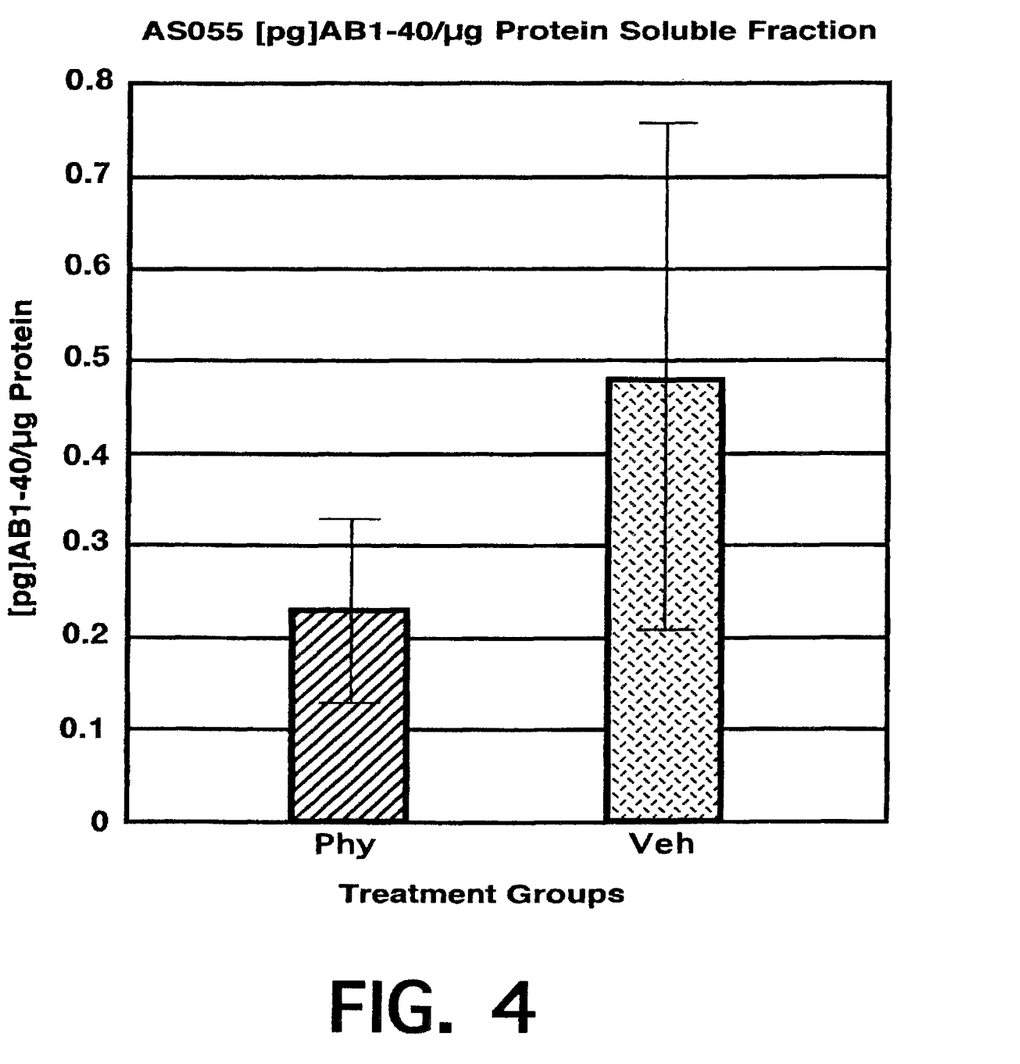
FIG. 4 is a chart of soluble amyloid beta 1-42/µg protein, phytic acid and a vehicle carrier.
Figure 5:
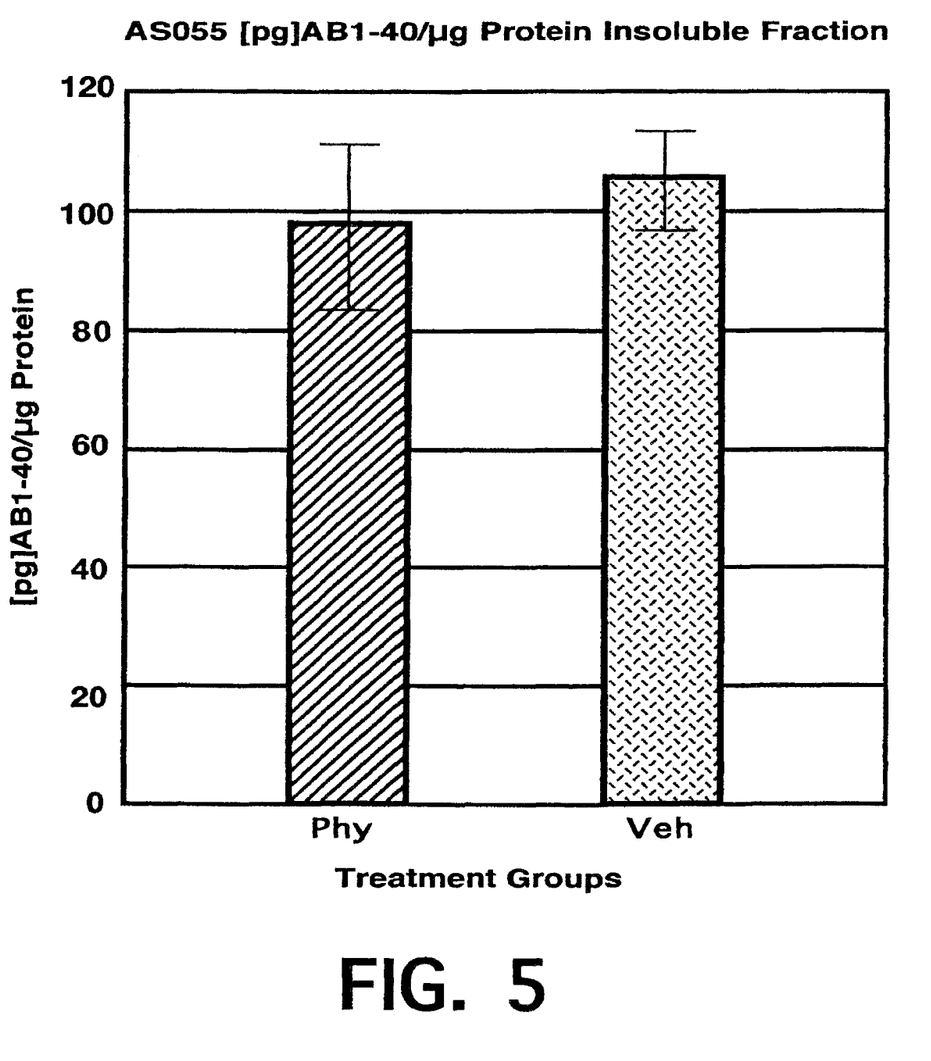
FIG. 5 is a chart of soluble amyloid beta—40/µg protein, phytic acid and a vehicle carrier.
Figure 6:
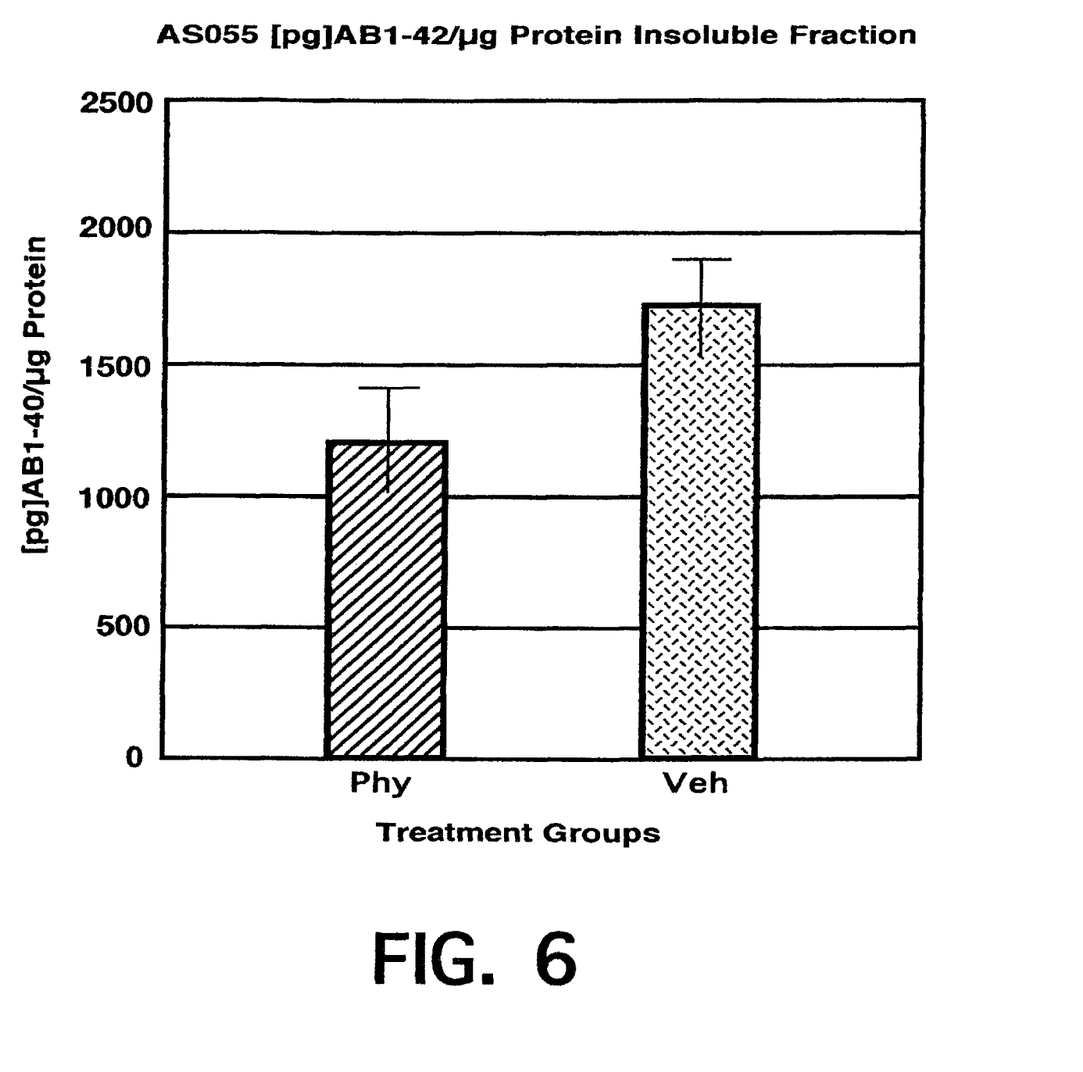
FIG. 6 is a chart of insoluble amyloid beta 1-42/µg protein, phytic acid and vehicle carrier.

Applicant also submits Table 1 and FIGS. 4-6 showing data from in vivo testing of the subject matter compounds in Alzheimer's transgenic mice. These Alzheimer's transgenic mice are genetically altered to produce Abeta plaque, and were treated for about six months with compounds of the Applicant's invention. Namely, the drinking water was infused with phytic acid so that the final concentration of phytic acid in the drinking water was 2%.

After six months, the animals were put down for autopsy and necropsy so that Abeta plaque in the brains was assayed, separated and weighed.

There was no toxicity from the phytic acid in the treated group, nor any significant weight loss.

RESULTS

The production of two different fractions of Abeta plaque insoluble species was lowered or reduced. One species of soluble Abeta plaque was lowered or reduced. All species tested were lowered or reduced, resulting in a complete in vivo success, without toxicity.

Table 1 is a tabulation of all results. FIGS. 4-6 are graphs comparing the tested compound in vivo with the control vehicle. In all three cases, there was a reduction in Abeta plaque after treatment with 2% phytic acid, compared to the control vehicle without phytic acid.

Key for Table 1 and FIGS. 4-6

Phy=IP6 at 2% phytic acid in mixed liquid drinking water with food

Veh=Negative control vehicle with laboratory food alone.

ID numbers=which animal was treated

TABLE 1

| ID # | Animal # | Tx | Genotype | AB 1-40 Dilution A | Dilution B | Results AB1-40 A | B | AB 1-42 Dilution A | Dilution B |
|---|---|---|---|---|---|---|---|---|---|
| 1 | 4562 | Phy | app | 16 | 200 | 2320.14 | 70486.195 | 2 | 3200 |
| 2 | 4563 | Phy | app | 16 | 200 | 2851.523 | 61486.942 | 2 | 3200 |
| 3 | 4578 | Phy | app | 16 | 200 | N/A | 30256.773 | 2 | 3200 |
| 4 | 4566 | Phy | app | 16 | 200 | 8.402 | 38495.306 | 2 | 3200 |
| 5 | 4570 | Phy | app | 16 | 200 | 1219.51 | 64667.238 | 2 | 3200 |
| 6 | 4631 | Phy | app | 16 | 200 | 1426.681 | 36921.948 | 2 | 3200 |
| 7 | 4567 | Phy | app | 16 | 200 | 358.289 | 33040.467 | 2 | 3200 |
| 8 | 4582 | Phy | app | 16 | 200 | 571.272 | 50066.569 | 2 | 3200 |
| 9 | 4564 | Veh | app | 16 | 200 | 13828.275 | 92831.01 | 2 | 3200 |
| 10 | 4559 | Veh | app | 16 | 200 | 2819.85 | 55137.189 | 2 | 3200 |
| 12 | 4579 | Veh | app | 16 | 200 | 19.911 | 34501.466 | 2 | 3200 |
| 13 | 4581 | Veh | app | 16 | 200 | 148.018 | 44625.892 | 2 | 3200 |
| 14 | 4617 | Veh | app | 16 | 200 | 1309.039 | 56358.841 | 2 | 3200 |
| 15 | 4575 | Veh | app | 16 | 200 | 560.149 | 53099.902 | 2 | 3200 |
| 16 | 4622 | Veh | app | 16 | 200 | 4527.412 | 62445.043 | 2 | 3200 |
| 17 | 4811 C | Veh | Wt | 4 | 3200 | N/A | N/A | 2 | 800 |
| 18 | 4809 C | Veh | App | 4 | 3200 | 144.004 | 1306162.415 | 2 | 800 |
| 19 | 4824 C | Veh | Wt | 4 | 3200 | N/A | N/A | 2 | 800 |
| 20 | 4811 H | Veh | Wt | 4 | 800 | N/A | N/A | 2 | 800 |
| 21 | 4809 H | Veh | App | 4 | 800 | 91.304 | 69277.345 | 2 | 800 |
| 22 | 4824 H | Veh | Wt | 4 | 800 | N/A | N/A | 2 | 800 |
| 23 | 4812 C | Veh | App | 4 | 3200 | 82.825 | 975775 | 2 | 800 |
| 24 | 4812 H | Veh | App | 4 | 800 | 48.566 | 16341 | 2 | 800 |
| 11 | 4561 | Veh | wt | 16 | 200 | N/A | N/A | 2 | 3200 |

| ID # | Results AB1-42 A | B | BCA Results Fraction A | Fraction B | [pg]AB1-40/µg Protein A | B | [pg]AB1-42/µg Protein A | B |
|---|---|---|---|---|---|---|---|---|
| 1 | N/A | 880713.806 | 5886.725 | 519.558 | 0.39413086 | 135.665691 | N/A | 1695.12125 |
| 2 | N/A | 698145.624 | 4147.397 | 577.817 | 0.68754522 | 106.412484 | N/A | 1208.24694 |
| 3 | N/A | 480036.365 | 2933.003 | 227.379 | N/A | 133.067579 | N/A | 2111.17282 |
| 4 | N/A | 705489.347 | 4586.985 | 455.21 | 0.0018317 | 84.5660377 | N/A | 1549.81074 |
| 5 | N/A | 207020.619 | 5216.961 | 491.504 | 0.2337587 | 131.570115 | N/A | 421.198238 |
| 6 | N/A | 703352.803 | 5967.692 | 687.425 | 0.23906747 | 53.710511 | N/A | 1023.17024 |
| 7 | N/A | 650661.541 | 6690.816 | 699.027 | 0.05354937 | 47.2663674 | N/A | 930.810313 |
| 8 | N/A | 528179.357 | 8193.309 | 604.247 | 0.06972421 | 82.8577866 | N/A | 874.111675 |
| 9 | N/A | 1349168.224 | 6846.047 | 670.862 | 2.01989192 | 138.375717 | N/A | 2011.09651 |
| 10 | N/A | 800295.049 | 6917.157 | 465.928 | 0.40766026 | 118.338432 | N/A | 1717.63674 |
| 12 | N/A | 772672.856 | 4740.048 | 413.594 | 0.00420059 | 83.4186811 | N/A | 1868.19165 |
| 13 | N/A | 983346.715 | 3521.983 | 395.894 | 0.04202689 | 112.721819 | N/A | 2483.86365 |
| 14 | N/A | 759029.968 | 6026.783 | 545.157 | 0.21720361 | 103.380936 | N/A | 1392.31445 |
| 15 | N/A | 947059.623 | 5533.192 | 542.265 | 0.10123433 | 97.9224217 | N/A | 1746.48857 |
| 16 | N/A | 659260.411 | 7442.838 | 723.057 | 0.60829108 | 86.3625454 | N/A | 911.768244 |
| 17 | N/A | 53327.115 | 7002.482 | 567.048 | N/A | N/A | N/A | 94.0433879 |
| 18 | N/A | 166553.084 | 7063.185 | 524.516 | 0.02038797 | 2490.22416 | N/A | 317.536708 |
| 19 | N/A | 90589.325 | 5218.073 | 394.671 | N/A | N/A | N/A | 229.531242 |
| 20 | N/A | 28596.199 | 5424.769 | 458.096 | N/A | N/A | N/A | 62.4240312 |
| 21 | N/A | 52953.772 | 5473.284 | 354.333 | 0.01668176 | 195.514798 | N/A | 149.446346 |
| 22 | N/A | 27824.951 | 6269.239 | 525.337 | N/A | N/A | N/A | 52.9659076 |
| 23 | N/A | 193869 | 6814.989 | 515.843 | 0.01215336 | 1891.61237 | N/A | 375.829467 |
| 24 | N/A | 78863 | 6097.491 | 510.065 | 0.00796492 | 32.0370933 | N/A | 154.613628 |
| 11 | N/A | N/A | 4052.036 | 332.112 | N/A | N/A | N/A | N/A |

| | [pg]AB1-40/µg Protein a | | b | | [pg]AB1-42/µg Protein a | | b |
|---|---|---|---|---|---|---|---|
| Phy | 0.23994 | Phy | 96.88957 | Phy | N/A | Phy | 1226.705 |
| Veh | 0.48579 | Veh | 105.7887 | Veh | N/A | Veh | 1733.051 |
| SE | a | SE | b | SE | a | SE | b |
| Phy | 0.09058 | Phy | 12.52249 | Phy | N/A | Phy | 189.3871 |
| Veh | 0.2683 | Veh | 7.258733 | Veh | N/A | Veh | 185.8261 |

Because of the unexpected finding that phytic acid lowers both soluble and insoluble Amyloid production in Alzheimer's transgenic mice, therefore it is reasonable that phytic acid will be useful in Amyloidosis an example of a protein aggregating Disease.

Furthermore, because the phytic acid and its related compounds disclose in vitro neuroprotective activity suggesting usefulness in treatment of Alzheimer's Disease, then it follows that the same compounds will be useful for treatment of motor neuron disease, or amyotrophic lateral sclerosis (ALS), in which the motor neurons unexplainably die off.

In the foregoing description, certain terms and visual depictions are used to illustrate the preferred embodiment.

However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention.

I claim:

1. A method consisting of the step of treating a person for an amyloidosis, aggregation of beta amyloid proteins and tau proteins in the brain, and/or a protein aggregating disease by orally administering an effective amount of at least one compound selected from the group consisting of phytic acid, salts of phytic acid, isomers of phytic acid and hydrolysates of phytic acid to said person, said effective amount being in a range of from 0.5 to 18.75 grams per day, and said effective amount being sufficient to protect from and/or attenuate said amyloid protein precursor C-terminal fragment (APP CTF)-induced neurotoxicity and associated beta amyloid plaque formation, thus preventing and/or treating said protein aggregating disease.

2. The method as defined in claim 1, wherein said person is treated for said Alzheimer's disease, and orally administering of said at least one compound protects from and/or attenuates said amyloid protein precursor C-terminal fragment (APP CTF)-induced neurotoxicity by suppressing oxidative stress associated with said amyloid protein precursor C-terminal fragment (APP CTF) induced neurotoxicity, and wherein said suppressing of said oxidative stress reduces soluble amyloid beta plaque production and/or insoluble beta plaque production in said brain of said person.

3. The method as defined in claim 2, wherein said range of said effective amount of said at least one compound is from 9 to 18.75 grams per day.

4. The method as defined in claim 2, wherein said range of said effective amount of said at least one compound is from 5 to 9 grams per day.

5. The method as defined in claim 1, wherein said person is treated for said amyloidosis.

6. The method as defined in claim 1, wherein said protein aggregating disease is amyotrophic lateral sclerosis (ALS).

7. The method as defined in claim 1, wherein said orally administering said at least one compound occurs when said person has an empty stomach.

8. The method as defined in claim 1, wherein said at least one compound is the only effective ingredient administered for protecting from and/or attenuating said amyloid protein precursor C-terminal fragment (APP CTF)-induced neurotoxicity.

9. The method as defined in claim 1, wherein said effective amount of said at least one compound is orally administered to said person in water.

10. The method as defined in claim 9, wherein a 2% water solution of said at least one compound is orally administered to said person each day in a volume that is sufficient to provide a daily dosage of from 0.5 to 18.75 grams of said at least one compound.

11. The method as defined in claim 1, wherein the step of orally administering said effective amount of said at least one compound is the only step performed to protect from and/or attenuate said amyloid protein precursor C-terminal fragment (APP CTF) induced neurotoxicity and said associated beta amyloid plaque formation.

12. A method of protecting from and/or attenuating amyloid protein precursor C-terminal fragment (APP CTF)-induced neurotoxicity in a person susceptible to and/or suffering from a protein aggregating disease, said method consisting of the step of transdermally or intradermally administering to said person an effective daily dosage of at least one compound selected from the group consisting of phytic acid, salts of phytic acid, isomers of phytic acid, and hydrolysates of phytic acid to said person, and said effective daily dosage of said at least one compound being sufficient to protect from and/or attenuate said amyloid protein precursor C-terminal fragment (APP CTF)-induced neurotoxicity and associated beta amyloid plague formation, thus preventing and/or treating said protein aggregating disease.

13. The method as defined in claim 12, wherein said administering is transdermal, said administering of said at least one compound is performed by applying a topical composition to skin of said person, and said topical composition contains said effective daily dosage of said at least one compound, and is in the form of a cream, an ointment, or a gel.

* * * * *